US00PP32819P2

(12) United States Plant Patent
Ranney

(10) Patent No.: US PP32,819 P2
(45) Date of Patent: Feb. 16, 2021

(54) ***RHODODENDRON* PLANT NAMED 'NCRX3'**

(50) Latin Name: *Rhododendron hybrida*
Varietal Denomination: NCRX3

(71) Applicant: Thomas Green Ranney, Arden, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/602,642

(22) Filed: Nov. 12, 2019

(51) Int. Cl.
*A01H 5/02* (2018.01)
*A01H 6/36* (2018.01)

(52) U.S. Cl.
USPC ..... Plt./239
CPC ..... *A01H 6/364* (2018.05)

(58) Field of Classification Search
USPC ..... Plt./239, 240
CPC ..... A01H 5/02
See application file for complete search history.

(56) References Cited

PUBLICATIONS https://farwestshow.com/wp-content/uploads/2019/06/NewVarieties2019.pdf; Jun. 2019; 2 pages.*

* cited by examiner

*Primary Examiner* — Kent L Bell
(74) *Attorney, Agent, or Firm* — Cassandra Bright

(57) ABSTRACT

A new and distinct cultivar of *Rhododendron* plant named 'NCRX3' is disclosed, characterized by compact plants producing abundant double pink flowers. Plants rebloom and exhibit cold-hardiness to at least USDA Zone 6B. The new cultivar is a *Rhododendron*, suitable for ornamental garden purposes.

2 Drawing Sheets

Latin name of the genus and species: *Rhododendron hybrida.*

Variety denomination: 'NCRX3'.

BACKGROUND OF THE INVENTION

The present invention comprises a new and distinct triploid hybrid *Rhododendron* cultivar hereinafter referred to by the cultivar name 'NCRX3'. The new cultivar is the result of a planned breeding program to develop *Rhododendron* cultivars with double flowers, compact plant forms, and better re-bloom. The crossing was made in 2011 in Mills River, N.C. 'NCRX3' was selected from a population of sister plants derived from controlled, hand pollinations between the seed parent, *Rhododendron* 'Susan Oliver' (unpatented) and pollen parent, *Rhododendron* 'H2009-273-028' (unpatented), in 2013.

The first asexual propagation of 'NCRX3' occured in 2013 by softwood cuttings at a research nursery in Mills River, N.C. 'NCRX3' roots readily from firm softwood cuttings treated with a basal dip of 5,000 ppm indole butyric acid (potassium salt) in water. 'NCRX3' has been found to retain its distinctive characteristics through successive asexual propagations over the course of 5 years.

SUMMARY OF THE INVENTION

The following are the unique combination of characteristics of this new cultivar when grown under standard horticultural practices at Mills River, N.C.

1. Profuse spring flower display.
2. Re-blooming in Summer into Fall.

3. Double pink flowers.
4. Cold hardiness to at least 0° F., USDA Zone 6B.
5. Compact habit.

COMPARISON TO PARENT VARIETIES

'NCRX3' is similar in most horticultural characteristics to the seed parent. Plants of the new cultivar 'NCRX3' however differ in the following:

1. The new variety has pink flowers, while the seed parent has white with lavender flowers.
2. The new variety has double flowers, while the seed parent has semi-double flowers.
3. The new variety is more intermediate in height, while the seed parent is more of a ground cover/prostrate.
4. The new variety re-blooms, while the seed parent does not.

'NCRX3' is similar in most horticultural characteristics to the pollen parent. Plants of the new cultivar 'NCRX3' however differ in the following:

1. The new variety has pink flowers, while the pollen parent has bright magenta flowers.
2. The new variety has double flowers, while the pollen parent has single flowers.
3. The new variety is a more compact plant than the pollen parent.

COMMERCIAL COMPARISON

'NCRX3' can be compared to the commercial variety *Rhododendron* 'RLH1-2P8', U.S. Plant Pat. No. 21,447. Plants of the new cultivar 'NCRX3' are similar to plants of 'RLH1-2P8' in most horticultural characteristics. Plants of the new cultivar 'NCRX3', however, differ in the following:

1. The new variety has lighter pink flowers than this comparator.
2. The new variety is a shorter, more compact plant than this comparator.

BRIEF DESCRIPTION OF THE PHOTOGRAPHS

'NCRX3' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Rhododendron*.

DETAILED BOTANICAL DESCRIPTION

Figure 1:
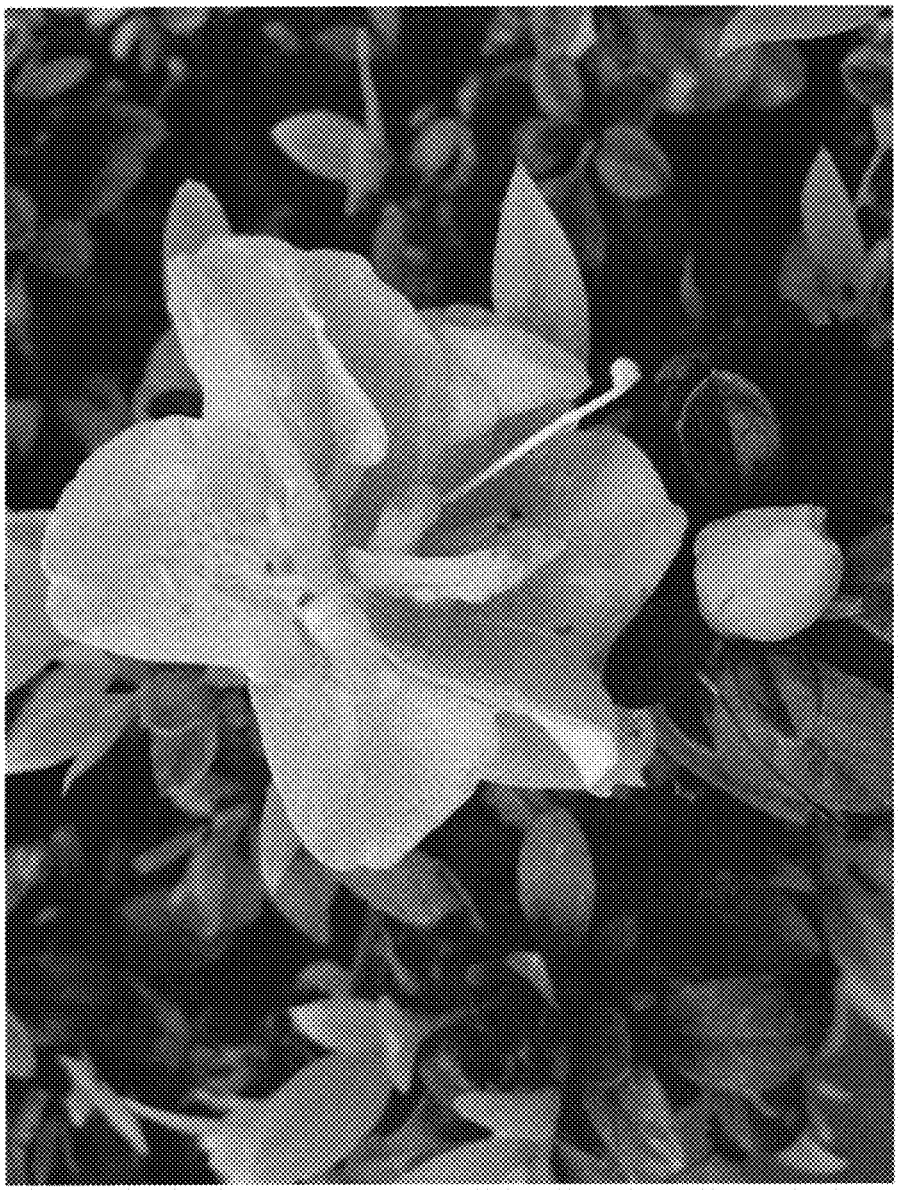
FIG. 1 shows the color of the expanding flower bud and individual flower of 'NCRX3' on a 3-year-old, container-grown plant in a greenhouse in Grand Haven, Mich. in 2019.
Figure 2:
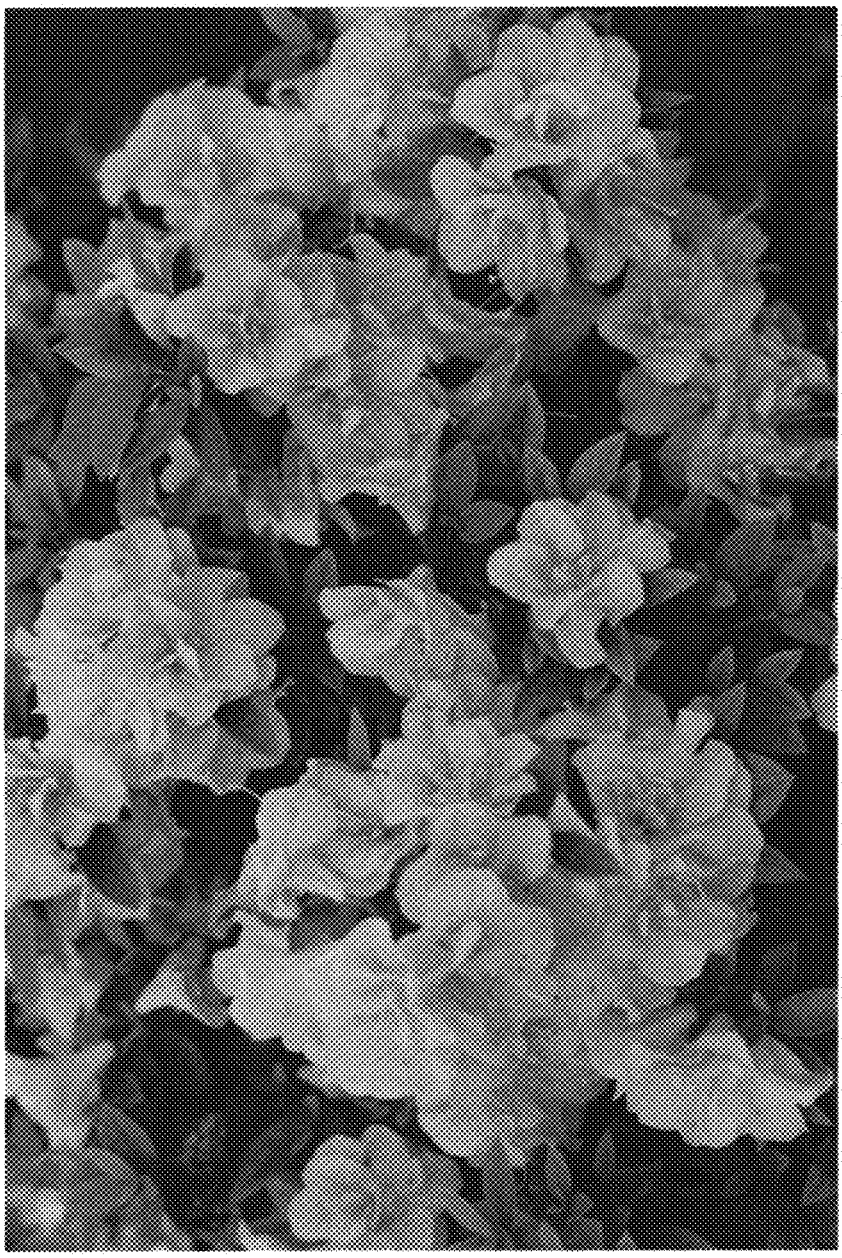
FIG. 2 shows a 3-year-old, container-grown plant in full bloom grown in a greenhouse in Grand Haven, Mich. in 2019.

The following is a detailed description of the botanical characteristics of the new and distinct hybrid *Rhododendron* known by the denomination 'NCRX3'. The detailed description was taken of a 3-year-old field-grown plant in Mills River, N.C., in 2019. For each measurable character, ten random measurements were recorded and used to derive averages and characteristic ranges. All colors cited herein refer to The Royal Horticultural Society Color Chart (R.H.S.), 2015 Edition. Where specific dimensions, sizes, colors, and other characteristics are described, it is to be understood that these were derived from 10-20 randomly selected measurable characters.

Botanical classification: *Rhododendron hybrida* 'NCRX3'.

PROPAGATION

Typically by firm softwood cuttings.

PLANT

Plant type: Evergreen shrub.
Growth habit: Compact and dense; spreading upwards.
Height: 50 cm.
Width: 90 cm.
Growth rate: Moderate, reaching a height and spread of 40 cm and 50 cm, respectively, after 3 years in container production.
Roots: Fibrous.
Shoots (new growth):
- *Shape*.—Rounded.
- *Color*.—A color between RHS Yellow-Green 144A and 144B mixed with Yellow-Green 146C and 146D, present individually in the mixture.
- *Texture*.—Pubescent.
- *Pubescence color*.—RHS Greyed-Orange N167.
- *Shoot diameter*.—Average 2.15 mm to 3 mm.
- *Shoot length*.—Variable, from 1 cm to 15 cm.
- *Stem aspect*.—0 to 45°.

Shoots (mature growth):
- *Shape*.—Rounded.
- *Color*.—Variable, generally falling within RHS Grey-Brown 199A and 199B, present individually with some woody stems exhibiting coloration more similar to a mix of Grey-Orange 174B, 174C and Greyed-Green 197A and 197B.
- *Texture*.—Pubescent.
- *Pubescence color*.—RHS Greyed-Orange N167A.
- *Length*.—Average 6 cm.
- *Diameter*.—Average 1.5 mm.
- *Stem aspect*.—0-45°.
- *Internode*.—Average range 2 cm to 5 cm.

Branching (mature growth):
- *Shape*.—Rounded.
- *Color*.—Variable, generally RHS Grey-Brown 199A and 199B. In some instances, slight exfoliation is observed with lower dermal layers exhibiting Grey-Orange 174C and 174D.
- *Texture*.—Pubescent.
- *Branch diameter*.—Average range 5.2 mm to 8 mm.
- *Branch length*.—Average range 10 cm to 30 cm.
- *Branching*.—Well branched.
- *Number of lateral branches*.—25 to 30.

FOLIAGE

Leaf:
- *Type*.—Evergreen to semi-evergreen.
- *Arrangement*.—Alternate.
- *Division*.—Simple.
- *Shape*.—Elliptic to obelliptic.
- *Apex*.—Young leaves are mucronate; older leaves are generally obtuse.
- *Base*.—Cuneate.
- *Margin*.—Entire, cilliate.
- *Venation*.—Reticulate.
- *Internode length*.—Average 7 mm.

Immature leaf:
- *Color*.—Upper surface: RHS Yellow-Green 144A. Lower surface: RHS Green 138B to Yellow-Green 145B.
- *Surface, upper and lower*.—Pubescent.
- *Pubescence color, upper and lower*.—RHS Green-White 157B.

Mature leaf:
- *Length*.—Average 2.6 cm.
- *Width*.—Average 1.5 cm.
- *Color*.—Upper surface: RHS Green NN137A to NN137D and Green 137A to 137D. Lower surface: RHS Green 138B to Yellow-Green N148A.
- *Surface, upper and lower*.—Slightly pubescent.
- *Fall/winter color*.—Upper surface: Mix of RHS Brown N200A and Yellow-Green 146A and 147A. Lower surface: RHS Yellow-Green 146A through 146C with occasional browning (Brown N200B, N200C and N200D).

Venation coloration:
- *Upper surface*.—RHS Green 137A.
- *Lower surface*.—RHS Green 138B.

Petiole:
- *Shape*.—Lunate.
- *Length*.—Average 6 mm.
- *Diameter*.—Average 1 mm to 1.5 mm.

*Texture*.—Upper surface: Glabrous. Lower surface: Pubescent, cilliate.

*Color*.—Upper surface: RHS Yellow-Green N144B. Lower surface: RHS Yellow-Green N144B. Pubescence: RHS Greyed-Orange 170C.

FLOWER

Inflorescence:

*Type*.—Congested terminal raceme (truss).

*Fragrance*.—None.

*Inflorescence/truss measurements at anthesis*.—Length: Average 7.5 cm. Width: Average 10.8 cm.

*Flowering season*.—Mid-spring (Late April-Early May) and then sporadically from July to September in Mills River, N.C.

*Flower number and consistency*.—'NCRX3' produce trusses on young plants the year following propagation. Flowers are typically present on most terminal shoots.

*Flowers per inflorescence*.—2-5 flowers per truss.

*Longevity of flowers*.—Individual flowers last 3-7 days. Opening is staggered within the individual flowers that comprise the truss. In field trials in Mills River 'NCRX3' bloom time lasts approximately 2-3 weeks, with peak bloom time (the time at which ~60% of the flowers are in bud or open) lasting approximately 1-2 weeks depending on environmental conditions. Reblooming behaviors are more sporadic.

*Self-cleaning or persistent*.—Persistent. Emerging shoots in the spring generally hide any remaining spent flowers.

Flowers:

*Truss bud*.—Color: RHS Yellow-Green 144D. Length: 1-1.5 cm. Diameter: 0.5-1 cm.

*Bud scales*.—Number: Variable, 3-7. Length: Approximately 1-1.5 cm. Width: Approximately 1 cm. Color: RHS Yellow-Green 144D upon opening; Yellow-Green 144D mixed with Orange-Red N34C at anthesis. Texture: Abaxial side is lightly pubescent; adaxial side is glabrous.

*Emerging floral bud*.—Shape: Obovate to elliptic, acuminate. Length: Average 2 to 3 cm. Diameter: Approximately 1 cm. Color: RHS Red-Purple 73B.

*Perianth* (*at anthesis*).—Diameter: Average 7 cm. Depth: Average 3 cm. Petal number: The first whorl generally contains 5 petals, and the inner whorl contains 4-7 petals with 2-10 petaloids. Aspect: Upward and outward-facing. Shape: Funnel-shaped. Attachment: Pedicellate.

Petals and petaloids: Generally, petals in the first and second whorls have similar dimensions and shapes, while petaloids can vary significantly in size and shape. Petals and petaloids are similar in color.

Petal:

*Length*.—Average 3 to 4 cm.

*Width*.—Average 2.5 to 3 cm.

*Shape*.—Obovate.

*Apex*.—Obtuse.

*Base*.—Obtuse.

*Margin*.—Slightly crenate.

*Fused or unfused*.—Fused at midpoint.

*Color*.—Petals and Petaloids: While opening: Upper surface: At the base petals/petaloids are lighter exhibiting a mix of RHS White N155C and gradually increasing in pigmentation in RHS Red-Purple 73D deepening along the edges to a mix of RHS Red-Purple 73C. Blotch: Generally present on 3 petals in both the first and second petal whorls, it is a mix of RHS Red 43C, Orange 26C and Green 143C while the flower is opening. Surface: Glabrous. Lower surface: Similar to adaxial surface color. Surface: Slightly pubescent. After opening: Upper surface: At the base petals/petaloids are a mix of RHS White N155C and Red-Purple 73C deepening at the tips to a mix of RHS Red-Purple 73B and 67B. Blotch: RHS Red-Purple 61B. Surface: Glabrous, silky and smooth. Lower surface: Similar to adaxial surface color. Surface: Glabrous, silky and smooth. Post-anthesis: Coloration is similar to that recorded at anthesis.

Petaloid:

*Shape*.—Highly variable. Observed shapes include: obovate, orbicular, elliptic, lanceolate. Many petaloids exhibit folding.

*Apex*.—Obtuse.

*Base*.—Acuminate/fused.

*Margin*.—Irregular, often lobed.

*Fused or unfused*.—Fused at midpoint.

Calyx/receptacle:

*Shape*.—Star-shaped.

*Arrangement*.—Single-whorl of persistent sepals.

Sepals:

*Number*.—5.

*Length*.—Approximately 1.5-2 mm.

*Width*.—Approximately 1.5-2.5 mm.

*Shape*.—Lanceolate.

*Apex*.—Acute.

*Margin*.—Entire.

*Fused or unfused*.—Fused at base.

*Color*.—RHS Yellow-Green 144B, both sides.

*Surface*.—Pubescent.

Pedicels:

*Shape*.—Rounded.

*Length*.—Average 3-5 mm.

*Diameter*.—Average 1 mm.

*Color*.—RHS Yellow-Green 144B.

*Surface*.—Adaxial surface sometimes smooth, abaxial surface may exhibit pubescence.

REPRODUCTIVE ORGANS

Most likely as an effect of petal doubling, reproductive characters, especially style length, stigmatic surface dimensions, stamen number, and anther dimensions can be highly variable. Many flowers exhibit stunted styles. Generally, flowers are both complete and perfect, although individual flowers may vary.

Gynoecium:

*Pistil number*.—1.

*Pistil length*.—Variable, generally 2-4 cm. Some pistils may exhibit twisting and fusion with stamens and petaloids.

*Pistil diameter*.—0.5-1 mm.

*Stigma shape*.—Generally orbicular.

*Stigma diameter*.—Approximately 1-1.3 mm.

*Stigma length*.—Approximately 1-1.3 mm.

*Stigma color*.—RHS Yellow-White 158A.

*Style length*.—Variable, 1-3 cm.

*Style diameter*.—Approximately 0.4-0.6 mm.
*Style color*.—RHS White 155B when opening, RHS Red-Purple 57A when receptive.
*Ovary shape*.—Rounded, tapering at the style union point.
*Ovary diameter*.—Approximately 2-3 mm.
*Ovary length*.—Approximately 3-4 mm.
*Ovary color*.—RHS Green 143B.
*Surface*.—Highly pubescent.
*Pubescence color*.—RHS White 155C.

Androecium:

*Stamen number*.—0 to 5.
*Anther shape*.—Ovoid with two apical pores.
*Anther attachment*.—Dorsifixed.
*Anther length*.—0.5-1.5 mm.
*Anther width*.—0.2-0.7 mm.
*Anther color*.—RHS Greyed-Orange 165B at anthesis.
*Filament length*.—Variable, 1-4 cm.
*Filament diameter*.—Approximately 0.3-0.5 mm.
*Filament color*.—RHS White 155B at base, fading to Red-Purple 75C toward anther union point.
*Amount of pollen*.—Extremely limited.
*Pollen type*.—Threadlike.
*Pollen color*.—RHS White 155A.

OTHER CHARACTERISTICS

Disease and pest resistance: Not observed to be susceptible nor resistant to normal diseases and pests of *Rhododendron*.

Temperature tolerance: Has been reliably cold hardy in USDA 6A.

Fruit/seed production:

*Fruit type*.—Capsule.
*Fruit texture*.—Highly pubescent.
*Fruit length*.—Approximately 4-6 mm.
*Fruit diameter*.—Approximately 2-3 mm.
*Fruit color*.—RHS Greyed-Orange 166B to 166D at maturity.
*Seed number*.—None observed.

What is claimed is:

1. A new and distinct cultivar of *Rhododendron* plant named 'NCRX3' as herein illustrated and described.

* * * * *